United States Patent [19]

Middelburg

[11] Plant 4,270

[45] Jun. 20, 1978

[54] CHRYSANTHEMUM

[75] Inventor: Nicolaas Middelburg, 's Gravenzande, Netherlands

[73] Assignee: Middleburg, B.V., 's Gravenzande, Netherlands

[21] Appl. No.: 820,920

[22] Filed: Aug. 22, 1977

[51] Int. Cl.[2] ..... A01H 5/00

[52] U.S. Cl. ..... Plt./74

[58] Field of Search ..... Plt./74

*Primary Examiner*—Robert E. Bagwill
*Assistant Examiner*—James R. Feyrer
*Attorney, Agent, or Firm*—Boone, Schatzel, Hamrick & Knudsen

[57] ABSTRACT

A new variety of chrysanthemum plant originating as a sport of Horim (unpatented) and characterized by satiny pure white blooms, vigorous growth, nine week response, permanence, and distinguished from the parent cultivar, Horim, by larger and purer white blooms.

1 Drawing Figure

BACKGROUND OF THE NEW PLANT

The present invention comprises a second, distinct cultivar of chrysanthemum plant which is a sport of the unpatented off-white chrysanthemum known as Horim. The new cultivar was discovered by Nicolaas Middelburg on Dec. 27, 1974, at 's Gravenzande in the Netherlands, and has been asexually reproduced by cuttings at the same location. The new cultivar has been found to retain its distinctive characteristics through successive propagations.

DESCRIPTION OF THE DRAWING

The accompanying drawing shows the unique characteristics of the new cultivar, the color being as nearly true as possible with color illustrations of this type. The photo shows the new cultivar in various stages of bloom.

DESCRIPTION OF THE NEW PLANT

The new cultivar is a short day response plant and, when grown in the vicinity of 's Gravenzande, Holland, has a response time of about 9 weeks. The new cultivar may be grown year round under greenhouse conditions.

In the description which follows, color references are made to the "Horticultural Colour Chart II" issued by the British Colour Council in collaboration with the Royal Horticultural Society. The following data is based on observations made at 's Gravenzande, Holland.

Botanical classification: *Chrysanthemum morifolium.*

Bud:
- *Size.*—Medium.
- *Form.*—Short with flat top.
- *Sepals.*—Smooth edge.
- *Calyx.*—Small, smooth, apple shape.

Color:
- *When sepals first divide.*—White.
- *When petals begin to unfurl.*—White.
- *Inside of petals when half blown.*—White.
- *Reverse of petals when half blown.*—White.

Bloom:
- *Size.*—Medium.

- *Fully expanded.*—7–8 centimeters.
- *Borne.*—Several together.
- *Stems.*—Medium, strong.
- *Form.*—Single (daisy).
- *Permanence.*—Excellent, 4 weeks.

Color:
- *Center of flower.*—Cyprus Green 59/1.
- *Base of petals.*—Agathia Green 60.
- *Inside of petals.*—Pure White.
- *Reverse of petals.*—Pure White.
- *Tonality from a distance.*—White.
- *Discoloration.*—None.

Petals:
- *Texture.*—Thick.
- *Appearance.*—Satiny.
- *Arrangement.*—Imbricated.
- *Persistence.*—Drop off cleanly.
- *Fragrance.*—Typical chrysanthemum.
- *Number.*—Normally 33–38.

Reproductive organs:
- *Stamen, anthers.*—Few, small.
- *Pollen.*—Cadmium Orange 8/1.
- *Arrangement.*—Tucked inside calyx.
- *Style.*—Columnar.
- *Length.*—Short, thin.
- *Stigmas.*—Dresden Yellow 64.
- *Ovaries.*—Enclosed in calyx.

Plant:
- *Growth.*—Vigorous.
- *Height.*—Medium, depending on culture.

Foliage:
- *Top side.*—Scheeles Green 860.
- *Size.*—Medium.
- *Quantity.*—Normal.
- *Ribs and veins.*—Ordinary.
- *Edge.*—Serrated.
- *Underside.*—Smooth, Scheeles Green 860/2.

I claim:

1. A new and distinct cultivar of chrysanthemum, substantially as described and pictured herein, characterized by its satiny pure white blooms, vigorous growth, nine week response and permanence.

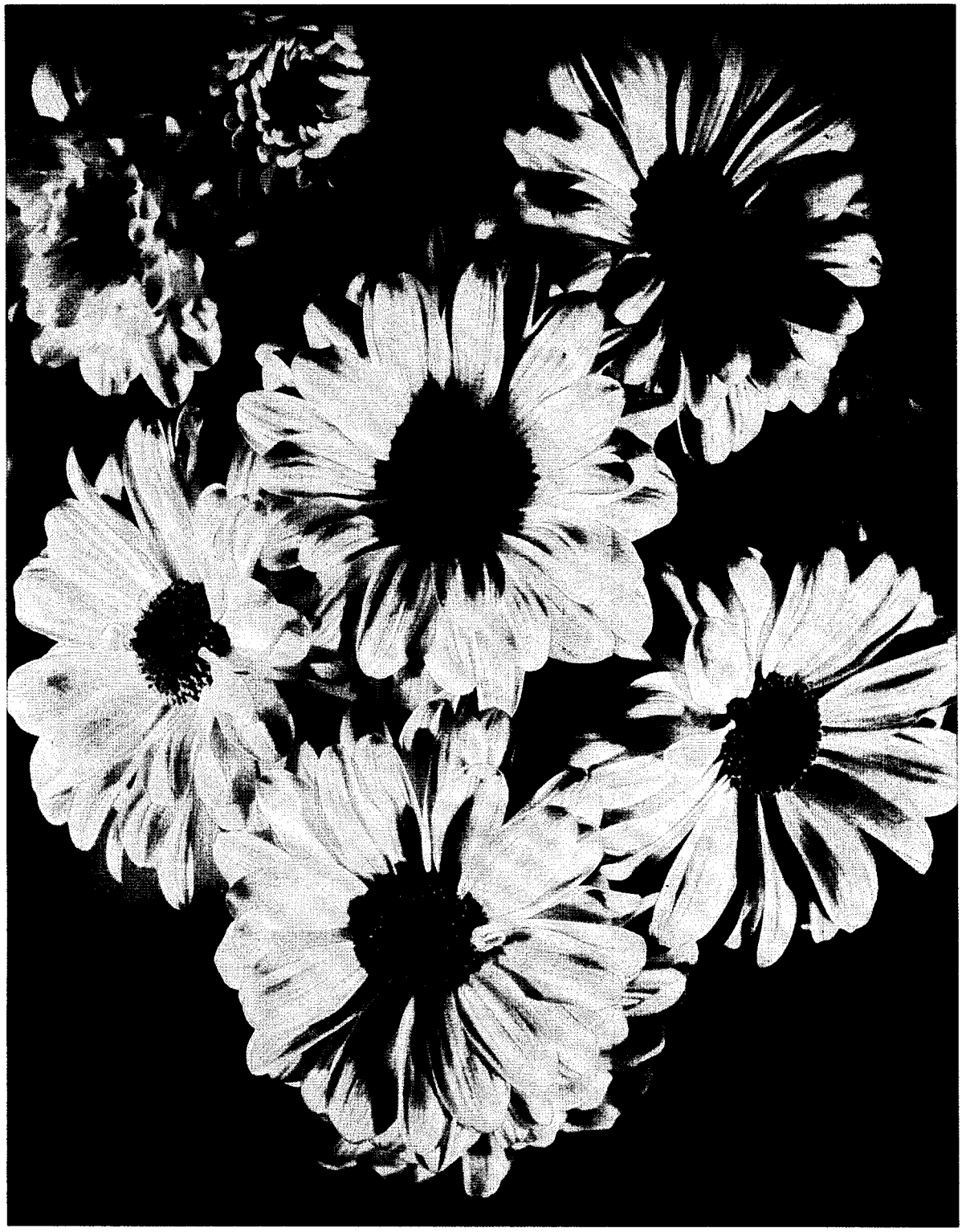

* * * * *